United States Patent
Hu et al.

(10) Patent No.: US 12,370,167 B2
(45) Date of Patent: Jul. 29, 2025

(54) BLOOD-BRAIN BARRIER PERMEABILITY REGULATOR AND USE THEREOF

(71) Applicant: ZHEJIANG UNIVERSITY, Hangzhou (CN)

(72) Inventors: Fuqiang Hu, Hangzhou (CN); Lijuan Wen, Hangzhou (CN); Hong Yuan, Hangzhou (CN); Kai Wang, Hangzhou (CN); Tingting Meng, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 1004 days.

(21) Appl. No.: 17/425,415

(22) PCT Filed: Jul. 8, 2019

(86) PCT No.: PCT/CN2019/095060
§ 371 (c)(1),
(2) Date: Jul. 23, 2021

(87) PCT Pub. No.: WO2020/151197
PCT Pub. Date: Jul. 30, 2020

(65) Prior Publication Data
US 2022/0096422 A1     Mar. 31, 2022

(30) Foreign Application Priority Data
Jan. 25, 2019 (CN) .......................... 201910073172.4

(51) Int. Cl.
*A61K 31/337* (2006.01)
*A61K 31/352* (2006.01)
(Continued)

(52) U.S. Cl.
CPC .......... *A61K 31/337* (2013.01); *A61K 31/352* (2013.01); *A61K 31/713* (2013.01); *A61K 47/64* (2017.08); *A61P 35/00* (2018.01)

(58) Field of Classification Search
CPC .. A61K 31/337; A61K 31/352; A61K 31/713; A61K 47/64; A61K 47/62; A61K 47/6907; A61K 2300/00; A61P 35/00
See application file for complete search history.

(56) References Cited

U.S. PATENT DOCUMENTS

| | | | |
|---|---|---|---|
| 9,006,197 B2 * | 4/2015 | Bumcrot | C12N 15/1136 514/44 A |
| 2008/0188480 A1 * | 8/2008 | Black | A61P 7/00 514/250 |

FOREIGN PATENT DOCUMENTS

CN     107880152 A     4/2018

OTHER PUBLICATIONS

Liu et al., Activation of Akt by SC79 decreased cerebral infarct in early cerebral ischemia-reperfusion despite increased BBB disruption, Neurosci. Lett., 681, pp. 78-82 (Year: 2018).*
(Continued)

*Primary Examiner* — Jeffrey S Lundgren
*Assistant Examiner* — Alexander K. Showalter
(74) *Attorney, Agent, or Firm* — Scully, Scott, Murphy & Presser, P.C.

(57) ABSTRACT

The present invention relates to use of SC79 or an analogue thereof in the preparation of a blood-brain barrier permeability regulator. The blood-brain barrier permeability regulator comprises SC79 or an analogue thereof as an active ingredient, which down-regulates expression of tight junction proteins Claudin-5 and Occludin by activating Claudin-5 and Occludin signaling pathway downstream the protein kinase B, and thereby increases the blood-brain barrier permeability, and enhances the efficiency of transportation of a brain targeting drug delivery system, especially, an Angiopep-2-modified glycolipid nano-delivery system, into the brain. The present invention also relates to a kit comprising the blood-brain barrier permeability regulator and a (Continued)

brain targeting drug delivery system. According to the present invention, use of the blood-brain barrier permeability regulator in combination with a brain targeting drug delivery system can enhance the efficiency of transportation of a brain targeting drug delivery system into the brain, and thereby improve the therapeutic efficacy of the brain targeting drug delivery system.

17 Claims, 8 Drawing Sheets

Specification includes a Sequence Listing.

(51) Int. Cl.
A61K 31/713 (2006.01)
A61K 47/64 (2017.01)
A61P 35/00 (2006.01)

(56) References Cited

OTHER PUBLICATIONS

Pinto et al., Targeted brain delivery nanoparticles for malignant gliomas, Nanomed., 12, pp. 59-72 (Year: 2017).*
Ganesh, T., et al., "Lead Optimization Studies of Cinnamic Amide EP2 Antagonists", J. Med. Chem. 2014, pp. 4173-4184, 57.
Hawkins, R.A., et al., "Structure of the Blood-Brain Barrier and Its Role in the Transport of Amino Acids", The Journal of Nutrition, 2006, pp. 218S-226S, 136.
Pardridge, W., et al., "Drug transport across the blood-brain barrier", Journal of Cerebral Blood Flow & Metabolism, (2012), pp. 1959-1972, 32.
International Search Report dated Oct. 10, 2019 issued in PCT/CN2019/095060.
Gerty Schreibelt et al. "Reactive Oxygen Species Alter Brain Endothelial Tight Junction Dynamics via RhoA, PI3 kinase, and PKB Signaling", The FASEB Journal, vol. 21, Nov. 30, 2007, pp. 3666-3676.

* cited by examiner

SEQUENCE LISTING

```
<160> NUMBER OF SEQ ID NOS: 2

<210> SEQ ID NO 1
<211> LENGTH: 21
<212> TYPE: RNA
<213> ORGANISM: Artificial Sequence
<220> FEATURE:
<223> OTHER INFORMATION: Synthetic nucleotide sequence
<220> FEATURE:
<221> NAME/KEY: misc_feature
<222> LOCATION: (20)..(21)
<223> OTHER INFORMATION: "n" is thymine ("t")

<400> SEQUENCE: 1
gucuaucagc gcagcuacun n                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic nucleotide sequence
<220> FEATURE:
<221> NAME/KEY: misc_feature
<222> LOCATION: (20)..(21)
<223> OTHER INFORMATION: n is thymine ("t")

<400> SEQUENCE: 2
aguagcugcg cugauagacn n                                              21
```

BLOOD-BRAIN BARRIER PERMEABILITY REGULATOR AND USE THEREOF

SEQUENCE LISTING

The instant application contains a Sequence Listing which has been submitted electronically in ASCII format and is hereby incorporated by reference in its entirety. Said ASCII copy, created on Feb. 20, 2025, is named 39860_ST25.txt and is 809 bytes in size.

TECHNICAL FIELD

The present invention belongs to the field of pharmaceuticals, and relates to use of SC79 or an analogue thereof in the preparation of a blood-brain barrier permeability regulator. The present invention also relates to use of the blood-brain barrier permeability regulator in combination with a brain targeting drug delivery system and a kit comprising the blood-brain barrier permeability regulator and a brain targeting drug delivery system.

BACKGROUND OF THE INVENTION

The blood-brain barrier (BBB), a special system for protecting and maintaining functions of the central nervous system, is mainly composed of brain microvascular endothelial cells, tight junctions between endothelial cells, basal lamina and glial cell podocytic process around capillaries, wherein the endothelial cells and tight junctions thereof are important morphological basis for the blood-brain barrier. Most macromolecular substances and more than 98% of small molecule drugs cannot leak through the blood-brain barrier, and only a minority of nutrients with a molecular weight of less than 500 Da can passively diffuse or selectively cross the blood-brain barrier to maintain a physiological balance of the central nervous system.

Loss of integrity of the blood-brain barrier is a significant pathological feature in occurrence and development of brain diseases. Brain capillary endothelial cells and the tight junctions expressed between the cells contribute to properties of low-osmotic and high-resistance of the blood-brain barrier. Among others, Claudin-5, Occludin and the like are key proteins forming the tight junctions, and play an important role in maintaining integrity of the blood-brain barrier.

On the other hand, in the treatment of brain diseases, especially brain tumors, drug therapy is usually demanded in supplement to surgical operation. However, presence of the blood-brain barrier greatly limits transportation of therapeutic drugs into the brain. There is an urgent need for solving of a key problem of how to effectively improve the efficiency of transportation of therapeutic drugs into the brain.

Recently, a series of progress has been made in the research of brain targeting drug delivery system. Among others, receptor-mediated trans-endocytosis is considered as one of the most effective pathways for brain targeting delivery due to its high affinity, selectivity and specificity. The blood-brain barrier expresses a large number of receptors, such as transferrin receptor, lipoprotein receptor, insulin receptor, acetylcholine receptor, diphtheria toxin protein receptor, folic acid receptor or the like, and modifies the surface of a nano-drug delivery system with a respective ligand (such as transferrin, monoantibody OX26, CDX polypeptide, RVG29 polypeptide, TGN polypeptide, Angiopep-2 polypeptide or the like). Once administered intravenously, the drug is transported into the brain across BBB via a receptor mediated pathway to improve the efficacy of drug therapy. Angiopep-2 is an aprotinin-derived polypeptide that targets specifically the low density lipoprotein receptor-associated protein 1. The low density lipoprotein receptor-associated protein 1 is highly expressed in both the blood-brain barrier and the glioma cell. Therefore, it can realize a dual targeting to both the blood-brain barrier and the glioma cell to modify Angiopep-2 onto the surface of a reduction responsive chitosan-octadecylamine graft.

It has been found that many central nervous system diseases may lead to a pathological destruction of the blood-brain barrier structure and an increase in the blood-brain barrier permeability. On the one hand, the increase in the blood-brain barrier permeability may cause an environmental unbalance in the central nervous system. On the other hand, the pathological destruction of the blood-brain barrier may also significantly enhance transportation of a brain targeting drug delivery system into the brain, and delivery of a therapeutic drug in the brain is increased. The brain targeting drug delivery system can be transported into the brain through a receptor-mediated pathway and a pathological window of the blood-brain barrier simultaneously, producing a more significant efficacy. So far, researches in the brain targeting drug delivery system mostly focus on interactions between a ligand and its receptor, and targeting cells and targeting tissues, while it is ignored that there may be a potential change in the pathological blood brain barrier function during the treatment of a disease with a delivery system. Mechanism related to the corresponding problem of reduced efficiency of penetration of the delivery system into the brain has not been thoroughly studied yet.

SC79 is a protein kinase B phosphorylation activator having a molecular formula of $C_{17}H_{17}ClN_2O_5$ and a molecular weight of 364.78, which may down-regulate expression of tight junction proteins Claudin-5 and Occludin by activating Claudin-5 and Occludin signaling pathway downstream the protein kinase B. An analogue of SC79 mainly refers to an activator having a mechanism similar to that of SC79 and acting on the protein kinase B, which down-regulates expression of tight junction proteins Claudin-5 and Occludin by activating Claudin-5 and Occludin signaling pathway downstream the protein kinase B.

Recently, it has been found that in a mouse model of permanent local cerebral ischemia, SC79 inhibits the activation of protein kinase B in the cytoplasm and reproduces the primary cellular function of the protein kinase B signaling, and thereby increases the survival of neurons. However, the role of SC79 or an analogue thereof in regulating an increase in the blood-brain barrier permeability, promoting the efficiency of transportation of a drug delivery system into the brain, and improving the efficacy of a brain targeting drug delivery system has not been reported. It has not been reported that a combined use of SC79 or an analogue thereof and a brain targeting drug delivery system can enhance the transportation efficiency of the brain targeting drug delivery system into the brain and improve the anti-glioma efficacy of the brain targeting drug delivery system.

SUMMARY OF THE INVENTION

The present inventors have found that the treatment of brain diseases such as brain tumors with a brain targeting drug delivery system may be accompanied with a recovery of the blood-brain barrier function, which reduces the efficiency of transportation of the brain targeting drug delivery system into brain and reduces the therapeutic efficacy. It may be one of the main reasons responsible for a failure in the treatment of brain diseases. Therefore, it is of great research significance and scientific value to explore the mechanism of regulation of the blood-brain barrier permeability and maintain opening of the blood brain barrier during the treatment for improving the therapeutic efficacy of the brain targeting drug delivery system.

Therefore, the object of the present intention is to provide a blood-brain barrier permeability regulator, which is capable of maintaining opening of the blood-brain barrier during the treatment with a brain targeting drug delivery system and improves the therapeutic efficacy of the brain targeting drug delivery system, as well as a combined use of the blood-brain barrier permeability regulator and a brain targeting drug delivery system.

After a thorough research, the present inventors have found that a protein kinase B (AKT) activator SC79 or an analogue thereof has a role of regulating the blood-brain barrier permeability, which may down-regulate expression of tight junction proteins Claudin-5 and Occludin by activating Claudin-5 and Occludin signaling pathway downstream the protein kinase B. Consequently, the SC79 or an analogue thereof may increase the blood-brain barrier permeability, enhance the efficiency of transportation of a brain targeting drug delivery system, especially, an Angiopep-2-modified glycolipid nano-delivery system, into the brain, and significantly improve the therapeutic efficacy of the brain targeting drug delivery system. On the basis of the above findings, the present invention has been accomplished. In particular, the present invention relates to the followings.

1. Use of SC79 or an analogue thereof in the preparation of a blood-brain barrier permeability regulator.
2. The use of item 1, characterized in that the blood-brain barrier permeability regulator is capable of increasing the blood-brain barrier permeability and enhancing the efficiency of transportation of a brain targeting drug delivery system into the brain.
3. The use of item 2, characterized in that the brain targeting drug delivery system is an Angiopep-2-modified glycolipid nano-delivery system.
4. The use of item 3, characterized in that the Angiopep-2-modified glycolipid nano-delivery system is an Angiopep-2-modified glycolipid nano-delivery system co-delivering paclitaxel and a siRNA.
5. The use of item 4, characterized in that the siRNA comprises a siRNA having a nucleotide sequence as follows:

```
sence strand:
                                  (SEQ ID NO: 1)
5'-GUCUAUCAGCGCAGCUACUTT-3', antisense strand:
                                  (SEQ ID NO: 2)
5'-AGUAGCUGCGCUGAUAGACTT-3'.
```

6. The use of any of items 1-5, characterized in that the blood-brain barrier permeability regulator down-regulates expression of tight junction proteins Claudin-5 and Occludin by activating Claudin-5 and Occludin signaling pathway downstream the protein kinase B, and thereby increasing the blood-brain barrier permeability.
7. The use of any of items 1-5, characterized in that a brain targeting drug delivery system is administered 0.5 hour after the administration of the blood-brain barrier permeability regulator.
8. The use of any of items 1-5, characterized in that a brain targeting drug delivery system is administered 24 hours after the administration of the blood-brain barrier permeability regulator.
9. A brain targeting drug delivery kit, characterized in comprising a combination of a blood-brain barrier permeability regulator and a brain targeting drug delivery system, wherein the blood-brain barrier permeability regulator comprises SC79 or an analogues thereof as an active ingredient, and is capable of increasing the blood-brain barrier permeability and enhancing the efficiency of transportation of the brain targeting drug delivery system into the brain.
10. The kit of item 9, characterized in that the brain targeting drug delivery system is an Angiopep-2-modified glycolipid nano-delivery system.
11. The kit of item 10, characterized in that the Angiopep-2-modified glycolipid nano-delivery system is an Angiopep-2-modified glycolipid nano-delivery system co-delivering paclitaxel and a siRNA.
12. The kit of item 11, characterized in that the siRNA comprises a siRNA having a nucleotide sequence as follows:

```
sence strand:
                                  (SEQ ID NO: 1)
5'-GUCUAUCAGCGCAGCUACUTT-3', antisense strand:
                                  (SEQ ID NO: 2)
5'-AGUAGCUGCGCUGAUAGACTT-3'.
```

13. The kit of any of items 9-12, characterized in that the blood-brain barrier permeability regulator down-regulates expression of tight junction proteins Claudin-5 and Occludin by activating Claudin-5 and Occludin signaling pathway downstream the protein kinase B, and thereby increasing the blood-brain barrier permeability.
14. The kit of any of items 9-12, characterized in being a kit for the treatment of glioma.
15. Use of a combination of a blood-brain barrier permeability regulator and a brain targeting drug delivery system in the manufacture of a brain targeting drug delivery kit, characterized in that the blood-brain barrier permeability regulator comprises SC79 or an analogues thereof as an active ingredient, and is capable of increasing the blood-brain barrier permeability and enhancing the efficiency of transportation of the brain targeting drug delivery system into the brain.
16. The use of item 15, characterized in that the brain targeting drug delivery system is an Angiopep-2-modified glycolipid nano-delivery system.
17. The use of item 16, characterized in that the Angiopep-2-modified glycolipid nano-delivery system is an Angiopep-2-modified glycolipid nano-delivery system co-delivering paclitaxel and a siRNA.
18. The use of item 17, characterized in that the siRNA comprises a siRNA having a nucleotide sequence as follows:

```
sence strand:
                                  (SEQ ID NO: 1)
5'-GUCUAUCAGCGCAGCUACUTT-3', antisense strand:
                                  (SEQ ID NO: 2)
5'-AGUAGCUGCGCUGAUAGACTT-3'.
```

19. The use of any of items 15-18, characterized in that the blood-brain barrier permeability regulator down-regulates expression of tight junction proteins Claudin-5 and Occludin by activating Claudin-5 and Occludin signaling pathway downstream the protein kinase B, and thereby increasing the blood-brain barrier permeability.

20. The use of any of items 15-18, characterized in that the brain targeting drug delivery kit is a kit for the treatment of glioma.

Effect of the Invention

The present invention can provide a blood-brain barrier permeability regulator comprising SC79 or an analogue thereof as an active ingredient, which can increase the blood-brain barrier permeability, enhance the efficiency of transportation of a brain targeting drug delivery system, especially, an Angiopep-2-modified glycolipid nano-delivery system, into the brain. By a combined use of the blood-brain barrier permeability regulator and a brain targeting drug delivery system, it is enabled to enhance the efficiency of transportation of a brain targeting drug delivery system into the brain, and thereby improve the therapeutic efficacy of the brain targeting drug delivery system in the treatment of brain diseases, and has a significantly superior technical effect.

DESCRIPTION OF THE FIGURES

FIG. 5 shows the result of the amount of Evans blue permeated into the brain as quantitatively detected by ultraviolet spectrophotometry (n=3).

FIG. 7 shows the result of the concentration of FITC-dextran in the outer chamber of Transwell as detected by a fluorescence spectrophotometer (n=3).

FIG. 8 shows the expression result of a tight junction protein Claudin-5/Occludin as observed by a laser confocal micoroscope.

DETAILED DESCRIPTION OF THE INVENTION

Figure 1:
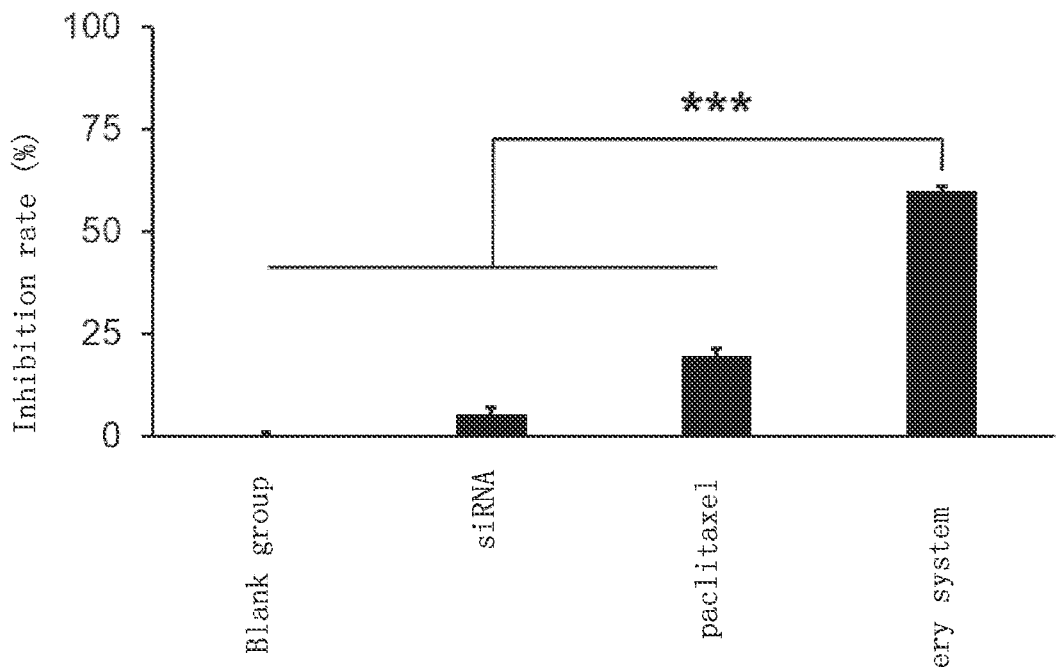
FIG. 1: In vitro cell inhibition rate against U87 MG glioma cells of the Angiopep-2-modified glycolipid nano-delivery system. 200 μL suspensions of well-grown U87 MG glioma cells were inoculated into a 96-well plate at a density of $5\times10^3$/well. After adherent growth of the cells, an Angiopep-2-modified glycolipid nano-delivery system was added, with paclitaxel at a concentration of 0.5 μg/mL and the siRNA at a concentration of 100 nM. The untreated cells were used as a blank control. The cell growth inhibition rate was measure with a tetrazolium blue colorimetric method (n=3).

The present invention relates to SC79 which is an activator of protein kinase B (AKT) having a molecular formula of $C_{17}H_{17}ClN_2O_5$ and a molecular weight of 364.78. SC79 is a protein kinase B phosphorylation activator, which may down-regulate expression of tight junction proteins Claudin-5 and Occludin by activating Claudin-5 and Occludin signaling pathway downstream the protein kinase B. It has been found that in a mouse model of permanent local cerebral ischemia, SC79 inhibits the activation of protein kinase B in the cytoplasm and reproduces the primary cellular function of the protein kinase B signaling, and thereby increases the survival of neurons.

An Analogue of SC79 mainly refers to an activator having a mechanism similar to that of SC79 and acting on the protein kinase B, which down-regulates expression of tight junction proteins Claudin-5 and Occludin by activating Claudin-5 and Occludin signaling pathway downstream the protein kinase B.

The present inventors have found that SC79 may down-regulate expression of tight junction proteins Claudin-5 and Occludin by activating Claudin-5 and Occludin signaling pathway downstream the protein kinase B. Therefore, SC79 can be used as an active ingredient of a blood-brain barrier permeability regulator. It has been further found that the blood-brain barrier permeability can be effectively increased 0.5-24 hours after the administration of SC 79, which significantly enhance the therapeutic efficiency of a brain targeting drug delivery system against a brain disease.

The brain disease includes, but is not limited to, glioma, pituitary tumor, meningioma, metastatic brain tumor or the like. Occurrence of each of those brain diseases may lead to loss of integrity of tight junctions of the blood-brain barrier and dysfunction of the barrier, which is accompanied with down-regulation of expression of proteins of the tight junctions, increase in the blood-brain barrier permeability, and environmental unbalance in the central nervous system.

As the brain targeting drug delivery system, a drug delivery system based on a receptor-mediated trans-endocytosis can be exemplified, such as, a brain targeting drug delivery system obtained by modifying the surface of a nano-drug delivery system with the respective ligand of a transferrin receptor, a lipoprotein receptor, an insulin receptor, an acetylcholine receptor, a diphtheria toxin protein receptor, a folic acid receptor, such as, transferrin, monoantibody OX26, CDX polypeptide, RVG29 polypeptide, TGN polypeptide, Angiopep-2 polypeptide or the like. Once administered intravenously, the brain targeting drug delivery system is transported into the brain across the blood-brain barrier via a receptor mediated pathway. Among others, Angiopep-2 is an aprotinin-derived polypeptide that specifically targets the low density lipoprotein receptor-associated protein 1. The low density lipoprotein receptor-associated protein 1 is highly expressed in both the blood-brain barrier and the glioma cell. Therefore, it can realize a dual targeting to both the blood-brain barrier and the glioma cell to modify Angiopep-2 onto the surface of a reduction responsive chitosan-octadecylamine graft.

In the present invention, the drug delivered by the Angiopep-2-modified glycolipid nano-delivery system is not particularly limited, provided as it is useful in the treatment of a brain disease. The therapeutic drug as used generally in this filed can be exemplified, such as, paclitaxel, doxorubicin or the like. A siRNA, plasmid DNA or the like may also be used. Any of these drugs may be used at alone, or two or more of them may be used in combination.

As a preferred example, in the present invention, the Angiopep-2-modified glycolipid nano-delivery system is an Angiopep-2-modified glycolipid nano-delivery system co-delivering paclitaxel and a siRNA.

As a more preferred example, in the present invention, the Angiopep-2-modified glycolipid nano-delivery system is an Angiopep-2-modified glycolipid nano-delivery system co-delivering paclitaxel and a siRNA which is useful in the treatment of glioma.

The above siRNA preferably comprises a siRNA having a nucleotide sequence as follows:

```
sence strand:
                                   (SEQ ID NO: 1)
5'-GUCUAUCAGCGCAGCUACUTT-3', antisence strand:
                                   (SEQ ID NO: 2)
5'-AGUAGCUGCGCUGAUAGACTT-3'.
```

By co-delivering paclitaxel and a siRNA having the above specific nucleotide sequence, the Angiopep-2-modified glycolipid nano-delivery system of the present invention has a significant therapeutic efficacy against glioma.

By applying the above blood-brain barrier permeability regulator in combination with a brain targeting drug delivery system, the present invention can enhance the efficiency of transportation of a brain targeting drug delivery system into the brain, and thereby improve the therapeutic efficacy of the brain targeting drug delivery system in the treatment of brain diseases, and has a significantly superior technical effect.

Preferably, the brain targeting drug delivery system is administered 0.5 hour, more preferably 12 hours, in particular preferably 24 hours, after the administration of the above blood-brain barrier permeability regulator. In addition, preferably, the brain targeting drug delivery system is administered 96 hours, more preferably 72 hours, in particular preferably 48 hours, before the administration of SC79. By applying SC79 within the above time range, it can more significantly enhance the efficiency of transportation of the brain targeting drug delivery system into the brain, and thereby improve the therapeutic efficacy of the brain targeting drug delivery system against a brain disease.

The brain targeting drug delivery kit of the present invention comprises a combination of the above blood-brain barrier permeability regulator and a brain targeting drug delivery system. The above blood-brain barrier permeability regulator comprises SC79 or an analogue thereof as an active ingredient, and is capable of increasing the blood-brain barrier permeability and enhancing the efficiency of transportation of the brain targeting drug delivery system into the brain. The brain targeting drug delivery system is preferably an Angiopep-2-modified glycolipid nano-delivery system, more preferably an Angiopep-2-modified glycolipid nano-delivery system co-delivering paclitaxel and a siRNA.

Preferably, the above siRNA comprises a siRNA having the following nucleotide sequence: sense strand 5'-GUCUAUCAGCGCAGCUACUTT-3' (SEQ ID NO: 1), antisense strand 5'-AGUAGCUGCGCUGAUAGACTT-3' (SEQ ID NO: 2). The brain targeting drug delivery kit of the present invention is preferably a kit for the treatment of glioma, which has a significant therapeutic efficacy against glioma.

In the followings, the present invention will be described in details with reference to Examples and the drawings. It should be noted that the following Examples are merely for illustration only, and do not limit the protection scope of the present invention.

EXAMPLES

Example 1 Preparation of an Angiopep-2-Modified Glycolipid Nano-Delivery System

1. Preparation of Micelles of an Angiopep-2-Modified Reduction Responsive Chitosan-Octadecylamine Graft Carrying Paclitaxel 10 mg of paclitaxel was accurately weighed and dissolved in anhydrous ethanol to prepare a 2.0 mg/ml of paclitaxel stock solution for later use. In accordance with a feeding amount of 5%~50%, the paclitaxel stock solution was added into a micellar solution of Angiopep-2-modified reduction responsive chitosan-octadecylamine graft at a concentration of 2.0 mg/mL while stirring. The resultant solution was stirred at room temperature for 30 minutes. After the reaction was completed, the reaction solution was subjected to a probe sonication for 20 times (200W, working for 2 seconds with intervals of 3 seconds). Subsequently, the reaction solution was transferred to a dialysis bag, and dialyzed against deionized water for 24 hours. The dialysate made to a constant volume was centrifuged at 8000 RPM for 10 minutes to remove the free paclitaxel. The supernatant was obtained to give the micelles of an Angiopep-2-targeted modified reduction responsive chitosan-octadecylamine graft carrying paclitaxel.

2. Preparation of an Angiopep-2-Modified Glycolipid Nano-Delivery System

The above obtained micellar solution of Angiopep-2-targeted modified reduction responsive chitosan-octadecylamine graft carrying paclitaxel was slowly mixed with 10 μM of siRNA solution at an N/P ratio of 150 (w/w). The resultant mixture was swirled in vortex, and then was left for 30 minutes to give an Angiopep-2-modified glycolipid nano-delivery system co-delivering paclitaxel and a siRNA, wherein the siRNA has the following nucleotide sequence: sense strand 5'-GUCUAUCAGCGCAGCUACUTT-3' (SEQ ID NO: 1), antisense strand 5'-AGUAGCUGCGCUGAUAGACTT-3' (SEQ ID NO: 2).

3. Cytotoxicity of the Angiopep-2-Modified Glycolipid Nano-Delivery System on U87 MG Glioma Cells U87 MG glioma cells were used as the model cell to assess the growth inhibitory effect of the Angiopep-2-modified glycolipid nano-delivery system on tumor cells with a tetrazolium blue colorimetric method. The Angiopep-2-modified glycolipid nano-delivery system was obtained according to the procedures as described in the above sections of 1 and 2. 200 μL suspensions of well-grown U87 MG cells were inoculated into a 96-well plate at a density of $5\times10^3$/well, and were incubated at 37° C. and 5% $CO_2$ until the cells adhere. The Angiopep-2-modified glycolipid nano-delivery system was added, with paclitaxel at a concentration of 0.5 g/mL and the siRNA at a concentration of 100 nM. The untreated cells were used as a blank control. Each of the group was repeated 3 times. After an incubation of 48 hours, 20 μL of 5 mg/mL thiazole blue was added to each of the wells, and was further incubated for 4 hours. The culture medium was removed. 200 μL of dimethyl sulfoxide was added to each of the wells. The 96-well plate was placed in a thermostat shaking box for 15 minutes. Absorbance at 570 nm was measured with a microplate reader. The cell inhibition rate was calculated according to the following equation:

Cell inhibition rate (%)=(1−absorbance value of a test group/absorbance value of a control group)×100%

The results were shown in FIG. 1, wherein the Angiopep-2-modified glycolipid nano-delivery system showed a cell inhibition rate of 60.0±1.1%, and the siRNA and paclitaxel showed a cell inhibition rate against U87 MG cells of 5.5±0.5% and 18.7±5.4%, respectively.

As can be seen from the results shown in FIG. 1, the Angiopep-2-modified glycolipid nano-delivery system can significantly inhibit the growth of glioma, and have a significant anti-glioma function with an effect significantly superior to the siRNA and paclitaxel.

4. Down-Regulation of Expression of Tumor Cell VEGF by the Angiopep-2-Modified Glycolipid Nano-Delivery System The Angiopep-2-modified glycolipid nano-delivery system was obtained according to the procedures as described in the above sections of 1 and 2. 2.0 mL suspensions of well-grown U87 MG cells were inoculated in a 6-well plate at a density of $4 \times 10^5$/well, and were incubated at 37° C. and 5% $CO_2$ until the cells adhere. The Angiopep-2-modified glycolipid nano-delivery system was added, with paclitaxel at a concentration of 0.5 µg/mL and the siRNA at a concentration of 100 nM. The incubation was carried out for 48 hours. The untreated cells were used as a blank control. Each of the group was repeated 3 times. The tumor cell VEGF expression level was measured with qt-PCR. The results were shown in FIG. 2.

Figure 2:
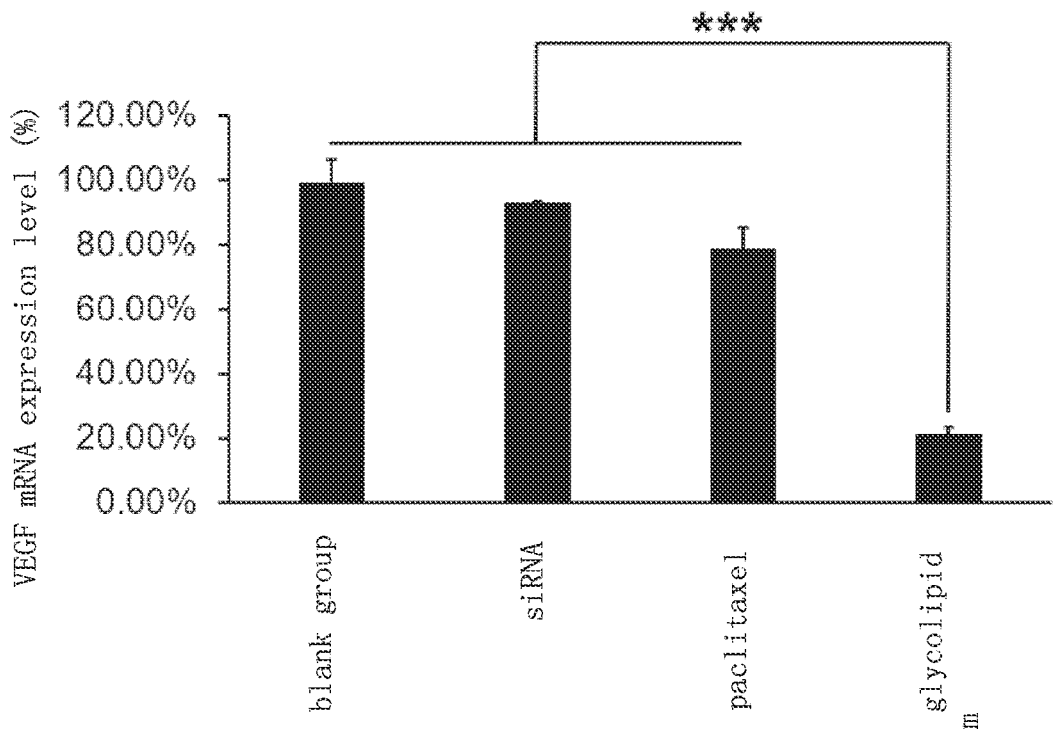
FIG. 2: In vitro down-regulation of expression of U87 MG cell VEGF mRNA by the Angiopep-2-modified glycolipid nano-delivery system. 2 mL suspensions of well-grown U87 MG glioma cells were inoculated into a 6-well plate at a density of $4\times10^5$/well. After adherent growth of the cells, an Angiopep-2-modified glycolipid nano-delivery system was added, with paclitaxel at a concentration of 0.5 μg/mL and the siRNA at a concentration of 100 nM. The incubation was carried out for 48 hours. An untreated group was used as the blank control. The RNA in the cells was extracted with TRIzol. The relative expression level of tumor cell VEGF mRNA was measure with qt-PCR and calculated with a ΔΔCt method (n=3).

As can be seen from the results shown in FIG. 2, the Angiopep-2-modified glycolipid nano-delivery system can significantly down-regulate the expression level of VEGF mRNA in the U87 MG tumor cells (21.1%), with an effect significantly superior to the siRNA (92.9%) and paclitaxel (78.5%).

Example 2 the Angiopep-2-Modified Glycolipid Nano-Delivery System Promotes In Vitro Function Recovery of a Pathological Blood-Brain Barrier 1. Construction of an In Vitro Model of Physiological Blood-Brain Barrier Brain microvascular endothelial cells bEnd.3 were used as model cells of a blood-brain barrier. 0.5 mL suspension of well-grown bEnd.3 cells was inoculated in the chamber of a 12-well Transwell plate with a pore size of 0.4 µm at a cell density of $1 \times 10^5$/well. 1.5 mL of fresh culture medium was supplemented in the outer chamber. The culture medium was refreshed every other day. Incubation was continued for 15 days at 37° C. and 5% $CO_2$. When the cell transmembrane resistance value was greater than 150 ohm·cm$^2$ ($\Omega \cdot cm^2$), it may be regarded that a model of physiological blood-brain barrier was obtained.

2. Construction of an In Vitro Model of Pathological Blood-Brain Barrier

U87 MG glioma cells were used as brain tumor model cells. 1.5 ml suspension of well-grown U87 MG cell suspension was inoculated in a 12-well plate at a cell density of $2 \times 10^5$/well. Incubation was carried out at 37° C. and 5% $CO_2$ until the cells adhere. Then, the physiological blood-brain barrier as constructed according to the procedure described in the above section of 1, i.e., the Transwell chamber with bEnd.3 cells grown, was transferred to the 12-well plate with U87 MG cells grown. Co-culture was continued for 24 hours to obtain a model of pathological blood-brain barrier.

3. The Angiopep-2-Modified Glycolipid Nano-Delivery System Promotes In Vitro Function Recovery of a Pathological Blood-Brain Barrier The pathological blood-brain barrier as constructed according to the procedure described in the above section of 2 was used as a model. The Angiopep-2-modified glycolipid nano-delivery system was added into the Transwell chamber in the model of pathological blood-brain barrier. After 48 hours of the drug action, the Transwell chamber with bEnd.3 cells grown was taken out, and washed with PBS for 3 times, fixed with 4% formaldehyde, and blocked with 10% bovine serum albumin for 30 minutes. Thereafter, Claudin-5/Occludin primary antibody was added, and was incubated at 4° C. overnight, and finally was incubated with fluorescently-labeled secondary antibody for 1 hour. The nucleus was counterstained with DAPI. Expression of tight junction protein Claudin-5/Occludin was observed with a laser confocal microscope. Expression level of Claudin-5/Occludin was semi-quantitatively analyzed with Image J. The Results were shown in FIG. 3.

Figure 3:
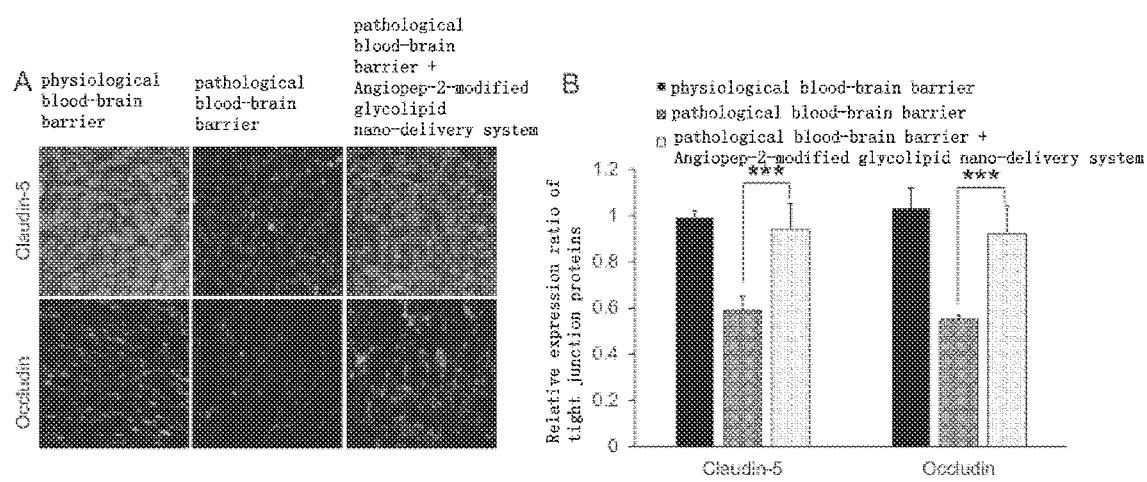
FIG. 3: In vitro down-regulation of expression of tight junction protein Claudin-5/Occludin and promotion of function recovery of the pathological blood-brain barrier by the Angiopep-2-modified glycolipid nano-delivery system. A Transwell model of brain microvascular endothelial cells bEnd.3 was used to mimic the physiological blood-brain barrier. A Transwell model of co-incubated brain microvascular endothelial cells bEnd.3 and glioma cell U87 MG was used to mimic the pathological blood-brain barrier. The Angiopep-2-modified glycolipid nano-delivery system was added into the Transwell chamber, with paclitaxel at a concentration of 0.5 μg/mL and the siRNA at a concentration of 100 nM. After an incubation of 48 hours, the bEnd.3 cells on the membrane of the Transwell chamber were immunofluorescence stained. Panel A shows the expression result of a tight junction protein Claudin-5/Occludin as observed by a laser confocal micoroscope. Panle B shows the result of fluorescence semi-quantitative analysis of Claudin-5/Occludin expression by Image J (n=3).

As can be seen from the results shown in FIG. 3, The Angiopep-2-modified glycolipid nano-delivery system can function to decrease down-regulation of expression of tight junction proteins Claudin-5/Occludin, and significantly reduce the degree to which the pathological blood-brain barrier is destructed. This indicates that the Angiopep-2-modified glycolipid nano-delivery system can promote in vitro function recovery of a pathological blood-brain barrier.

Example 3 the Angiopep-2-Modified Glycolipid Nano-Delivery System Promotes Function Recovery of a Pathological Blood-Brain Barrier in a Glioma Model Animal Male BABL/c nude mice (20+2 g) were used as the model animals. U87-luci glioma cells expressing luciferase were inoculated in the striatum area of nude mice at a concentration of $5 \times 10^5$ cells/5 µL by means of a brain stereotaxic instrument (inoculation coordinates, 0.8 mm on the anterior side of bregma, 2 mm on the right side, and 3 mm in depth), to construct an in situ glioma model. The Angiopep-2-modified glycolipid nano-delivery system was injected into tail veins at an administration dose of 10 mg/kg in terms of paclitaxel and 50 nM/kg in terms of siRNA. After 48 hours, an Evans blue solution was injected into tail veins at an administration dose of 5 mg/kg. After 4 hours, the intact brain of the nude mice was taken by cardiac perfusion. The distribution intensity of Evans blue in the brain tissue was qualitatively observed with a small animal live imaging instrument. The Results were shown in FIG. 4. The Evans blue was extracted from the brain tissue with an organic solvent of N,N-dimethylformamide. The amount of Evans blue permeated into the brain was quantitatively detected by ultraviolet spectrophotometry. The results were shown in FIG. 5.

Figure 4:
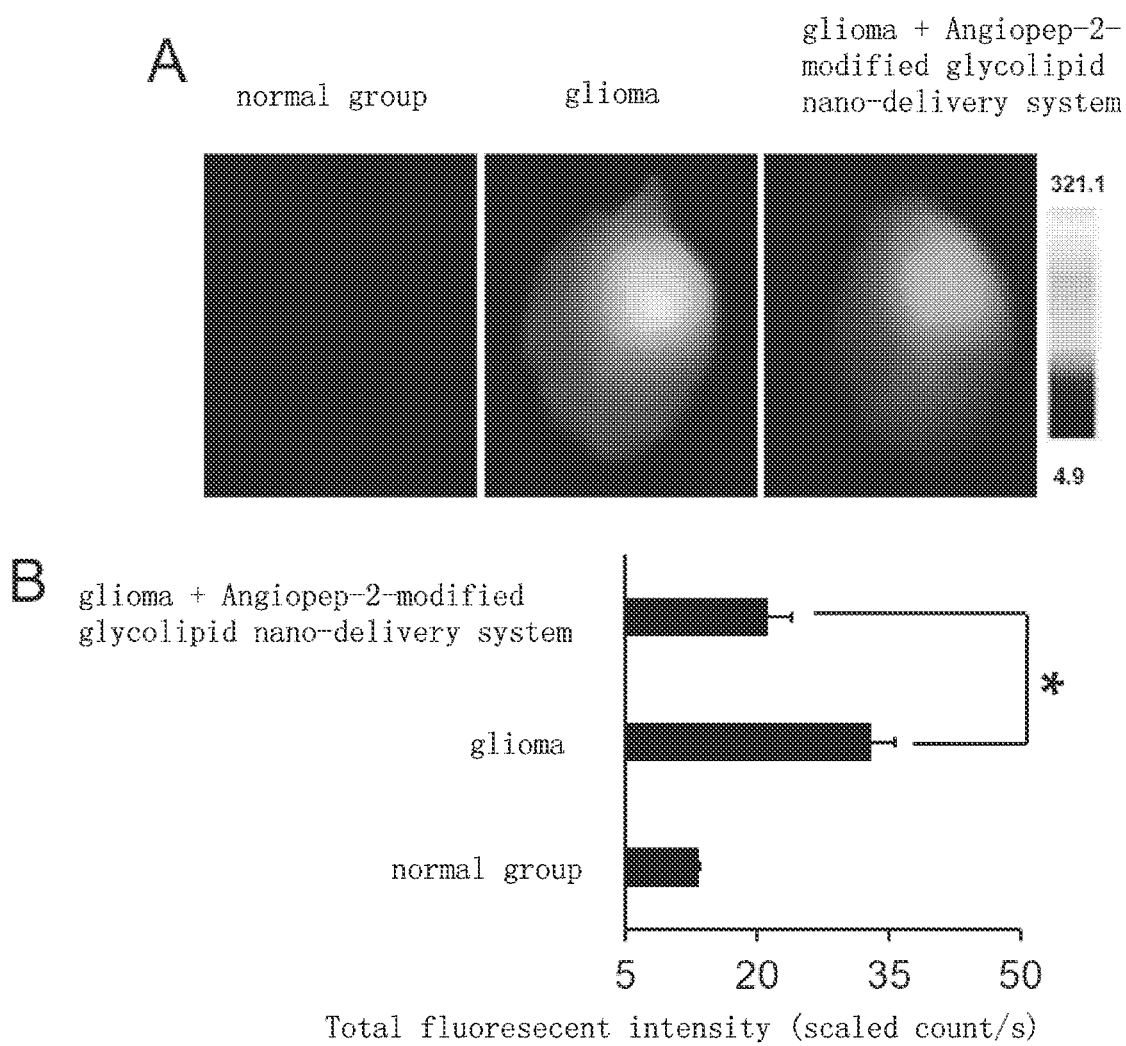
FIG. 4: Promotion of function recovery of the pathological blood-brain barrier and reduction in the blood-brain barrier permeability by the Angiopep-2-modified glycolipid nano-delivery system in a glioma model. The Angiopep-2-modified glycolipid nano-delivery system was injected into tail veins at an administration dose of 10 mg/kg in terms of paclitaxel and 50 nM/kg in terms of siRNA. After 48 hours, an Evans blue solution was injected into tail veins at an administration dose of 5 mg/kg. After 4 hours, the intact brain of the nude mice was taken by cardiac perfusion. Panel A shows the result of distribution intensity of Evans blue in the brain tissue as qualitatively observed with a small animal live imaging instrument. Panel B shows the semi-quantitative result of fluoresecent signal of Evans blue (n=3).
Figure 5:
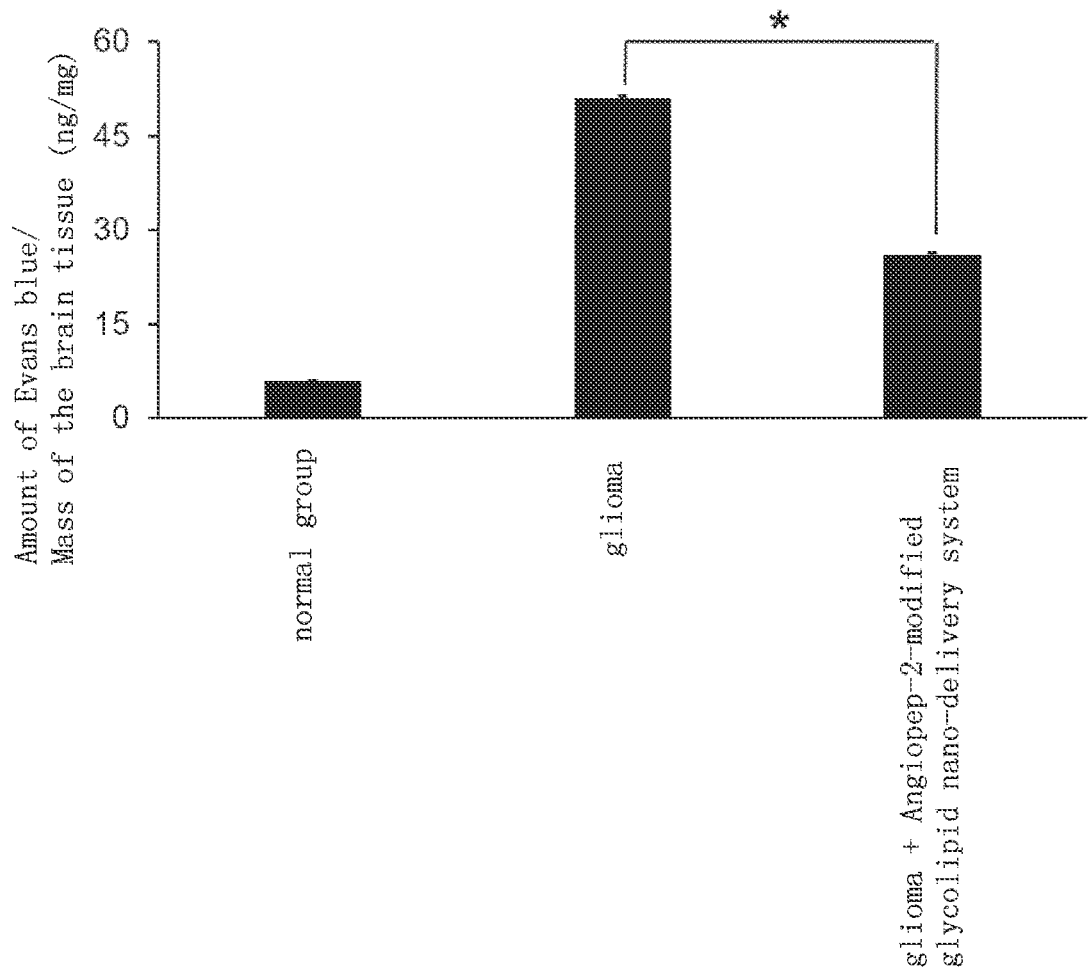
FIG. 5: Promotion of function recovery of the pathological blood-brain barrier and decrease in the amount of Evans blue permeated into the brain by the Angiopep-2-modified glycolipid nano-delivery system in a glioma model. The Angiopep-2-modified glycolipid nano-delivery system was injected into tail veins at an administration dose of 10 mg/kg in terms of paclitaxel and 50 nM/kg in terms of siRNA. After 48 hours, an Evans blue solution was injected into tail veins at an administration dose of 5 mg/kg. After 4 hours, the intact brain of the nude mice was taken by cardiac perfusion. The Evans blue was extracted from the brain tissue with an organic solvent of N,N-dimethylformamide.

As can be seen from the results shown in FIGS. 4 and 5, as compared with the tumor-bearing control group, after the administration of the Angiopep-2-modified glycolipid nano-delivery system, the amount of Evans blue permeated into the brain is decreased, which shows that the blood-brain barrier permeability is reduced. It indicates that the Angiopep-2-modified glycolipid nano-delivery system can reduce the blood-brain barrier permeability, and promote function recovery of the blood-brain barrier in a glioma model animal.

Example 4 SC79 Activates the Signaling Downstream the Protein Kinase B in a Dose-Dependent Manner, Promotes Down-Regulation of Tight Junction Proteins, and Increase the Blood-Brain Barrier Permeability The physiological blood-brain barrier as constructed according to the procedure described in the above section of 1 of Example 2 was used as a model.

A protein kinase B activator SC79 at different concentrations (0, 5 µg/mL, 10 µg/mL) was added into the Transwell chamber in the model of physiological blood-brain barrier. After 24 hours of the drug action, the Transwell chamber with bEnd.3 cells grown was transferred to another 12-well plate, and washed with PBS for 3 times. 0.5 mL of HBSS nutrient solution was added to the chamber, and the outer chamber was supplemented with 1.5 mL HBSS nutrient solution. After the cells were equilibrated at 37° C. for 15 minutes, the cell transmembrane resistance was detected by a cell resistance meter. The results are shown in FIG. 6.

A protein kinase B activator SC79 at different concentrations (0, 5 g/mL, 10 µg/mL) was added into the Transwell chamber in the model of physiological blood-brain barrier. After 24 hours of the drug action, the Transwell chamber with bEnd.3 cells grown was transferred to another 12-well plate, and washed with PBS for 3 times. A solution of dextran having a molecular weight of 10 kDa, which is fluorescently-labeled by a FITC-label, in HBSS was added to the chamber, and the outer chamber was supplemented with 1.5 mL HBSS nutrient solution. After the cells were incubated at 37° C. in the dark for 4 hours, the concentration of FITC-dextran transferred to the outer chamber via the Transwell chamber was detected with a fluorescence spectrophotometer. The results were shown in FIG. 7.

A protein kinase B activator SC79 at different concentrations (0, 5 µg/mL, 10 µg/mL) was added into the Transwell chamber in the model of physiological blood-brain barrier. After 24 hours of the drug action, the Transwell chamber with bEnd.3 cells grown was taken out, and washed with PBS for 3 times, then fixed with 4% formaldehyde, and blocked with 10% bovine serum albumin for 30 minutes. Thereafter, Claudin-5/Occludin primary antibody was added, and was incubated at 4° C. overnight, and finally was incubated with fluorescently-labeled secondary antibody for 1 hour. The nucleus was counterstained with DAPI. Expression of tight junction protein of Claudin-5/Occludin was observed with a laser confocal microscope. The Results were shown in FIG. 8.

Figure 6:
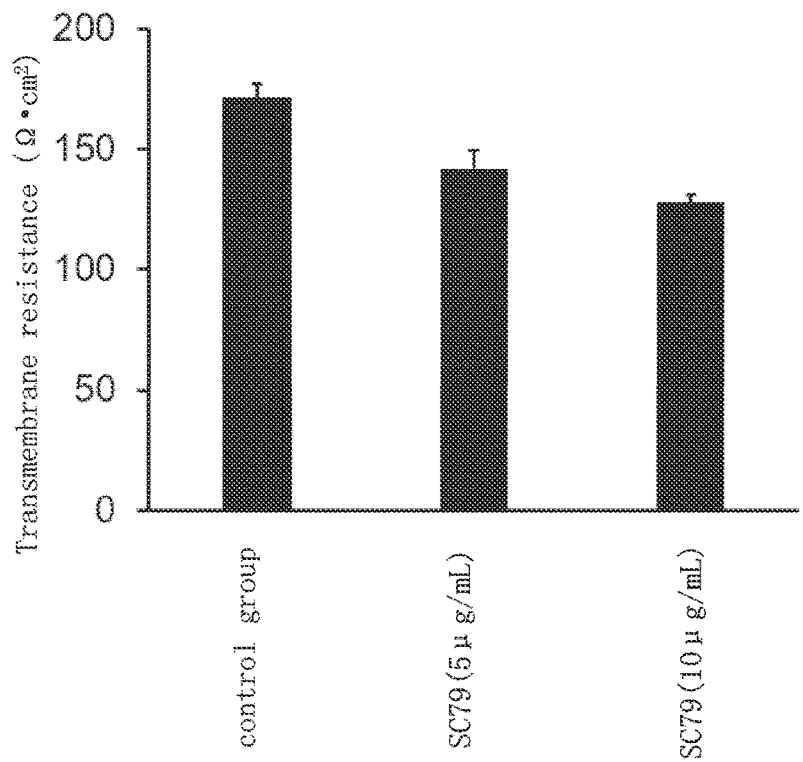
FIG. 6: In vitro dose-dependent regulation of transmembrane resistance of the blood-brain barrier by SC79. A Transwell model of brain microvascular endothelial cells bEnd.3 was used to mimic the physiological blood-brain barrier. SC79 at different concentrations (0, 5 μg/mL, 10 μg/mL) was applied to the Transwell chamber. After 24 hours, the cell transmembrane resistance was detected by a cell resistance meter (n=5).
Figure 7:
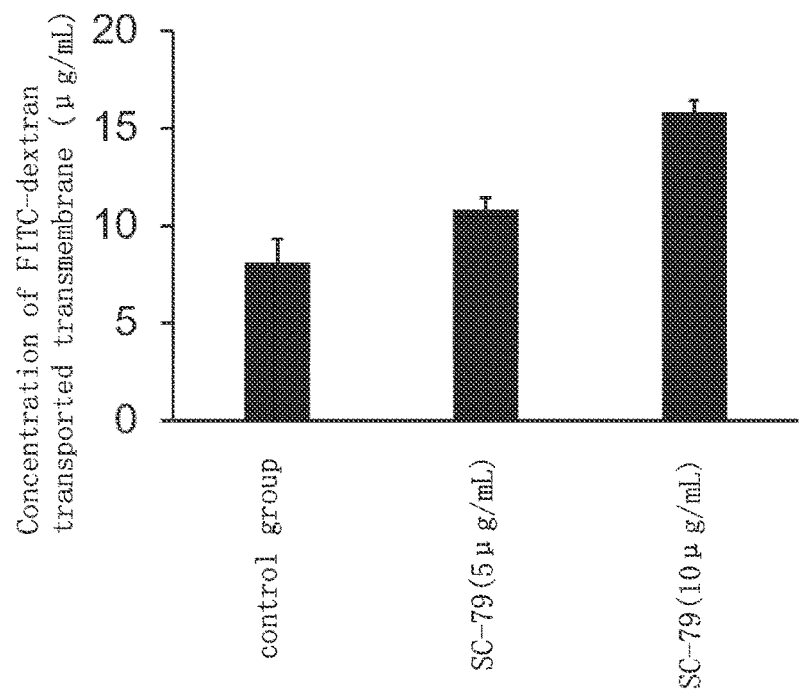
FIG. 7: In vitro dose-dependent influence of SC79 on the efficiency of transportation of FITC-dextran cross the blood-brain barrier. A Transwell model of brain microvascular endothelial cells bEnd.3 was used to mimic the physiological blood-brain barrier. SC79 at different concentrations (0, 5 μg/mL, 10 μg/mL) was applied to the Transwell chamber. After 24 hours, the Transwell chamber and the outer chamber were washed with PBS. A solution of FITC-dextran in HBSS was added to the Transwell chamber for an action of 4 hours.
Figure 8:
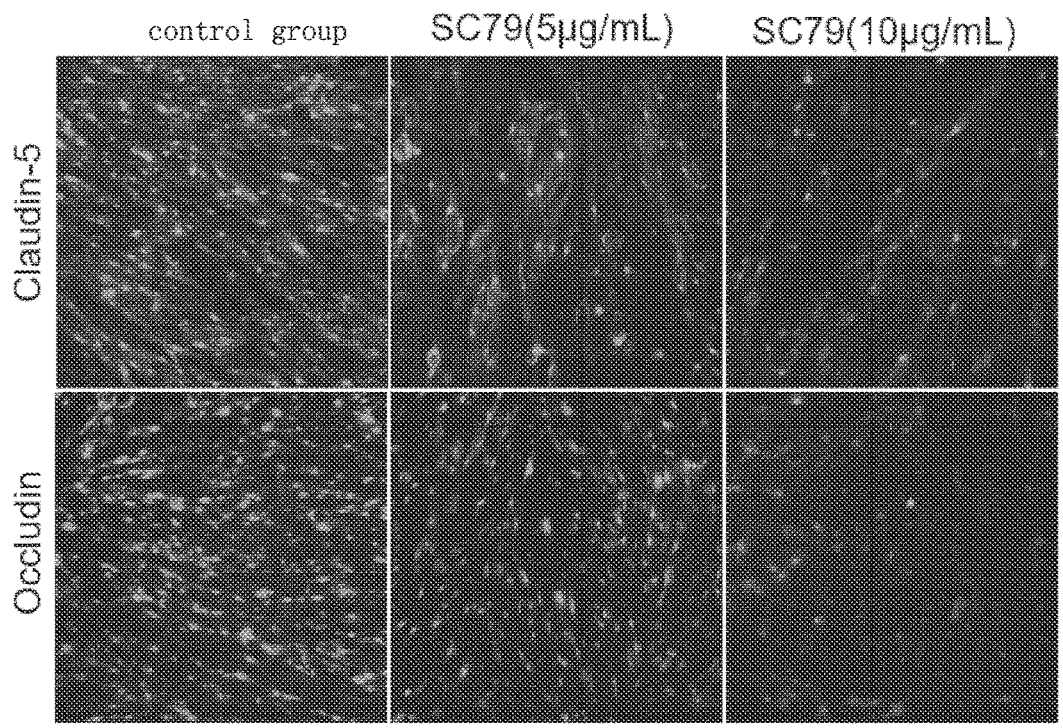
FIG. 8: In vitro dose-dependent down-regulation of expression of tight junction proteins Claudin-5/Occludin by SC79. A Transwell model of brain microvascular endothelial cells bEnd.3 was used to mimic the physiological blood-brain barrier. SC79 at different concentrations (0, 5 μg/mL, 10 μg/mL) was applied to the Transwell chamber. After 24 hours, the bEnd.3 cells on the membrane of the Transwell chamber were immunofluorescence stained.

As can be seen from the results shown in FIGS. 6, 7 and 8, SC79 activates the signaling downstream the protein kinase B in a dose-dependent manner, promotes down-regulation of expression of tight junction proteins, and increase the blood-brain barrier permeability.

Example 5 SC79 Activates the Signaling Downstream the Protein Kinase B in a Time-Dependent Manner, Promotes Down-Regulation of Tight Junction Proteins, and Increase the Blood-Brain Barrier Permeability The physiological blood-brain barrier and the pathological blood-brain barrier, as respectively constructed according to the procedures described in the above sections of 1 and 2 of Example 2, were used as a model, respectively. SC79 (5 µg/mL) was added into the Transwell chamber in the models of physiological blood-brain barrier and pathological blood-brain barrier for stimulus, respectively. The cell transmembrane resistance was real-time monitored. The results are shown in FIG. 9.

Figure 9:
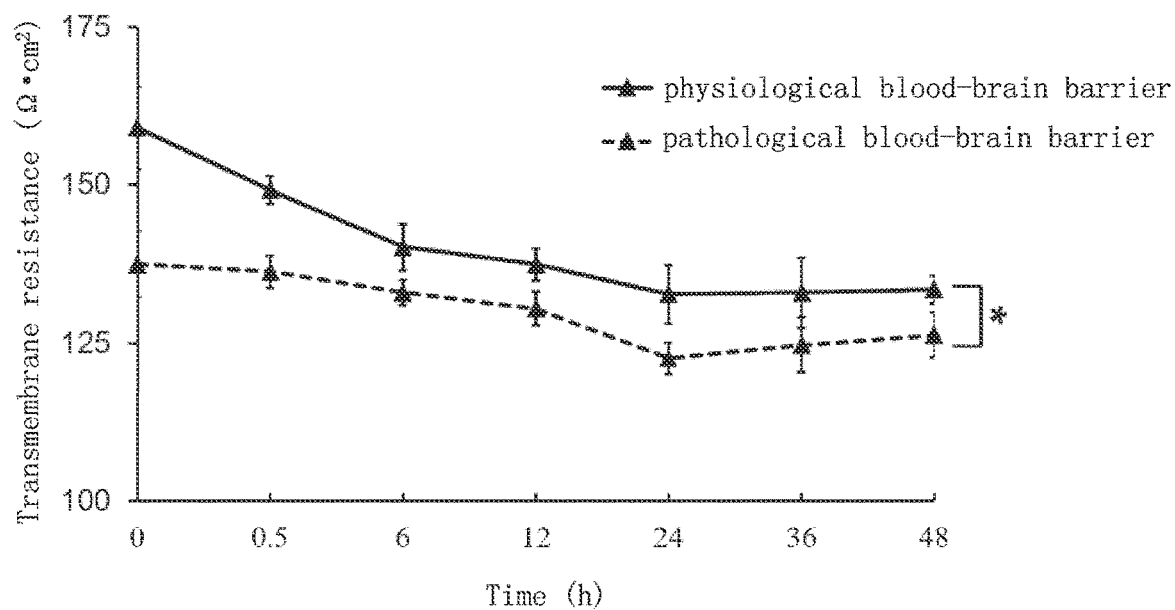
FIG. 9: In vitro time-dependent regulation of transmembrane resistance of the blood-brain barrier by SC79. A Transwell model of brain microvascular endothelial cells bEnd.3 was used to mimic the physiological blood-brain barrier. A Transwell model of co-incubated brain microvascular endothelial cells bEnd.3 and glioma cell U87 MG was used to mimic the pathological blood-brain barrier. SC79 (5 µg/mL) was applied to the Transwell chamber. The cell transmembrane resistance was real-time monitored by a cell resistance meter (n=5).

As can be seen from the results shown in FIG. 9, after the SC79 stimulus, the cell transmembrane resistance is decreased in a time-dependent manner, and the blood-brain barrier permeability is increased in a dose-dependent manner. After 24 hours of the drug action, SC79 has the most significant effect in increasing the blood-brain barrier permeability.

Example 6 SC79 Increases the Blood-Brain Barrier Permeability in a Glioma Model Animal, and Enhances Transportation of Angiopep-2-Modified Glycolipid Nano-Delivery System into the Brain Male BABL/c nude mice (20+2 g) were used as the model animals. SC79 diluted with 0.2% injection grade Tween 80 solution was injected into tail veins at an administration dose of 5 mg/kg, 10 mg/kg. After 24 hours, an Evans blue solution was injected into tail veins at an administration dose of 5 mg/kg. After 4 hours, the intact brain of the nude mice was taken by cardiac perfusion. The distribution intensity of Evans blue in the brain tissue was qualitatively observed with a small animal live imaging instrument. The Results were shown in FIG. 10.

Figure 10:
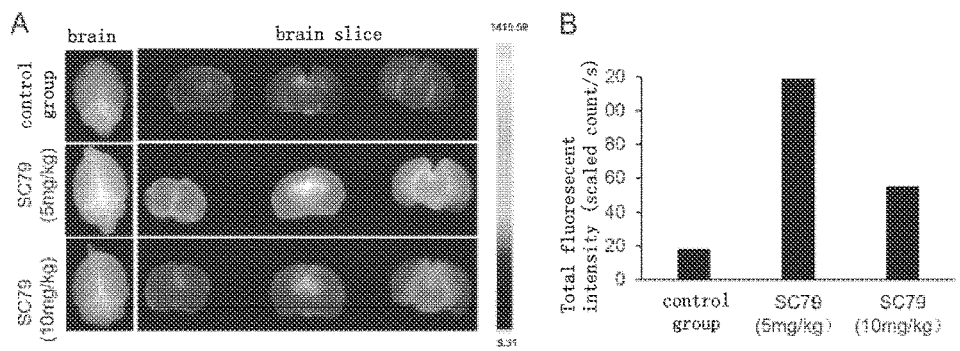
FIG. 10: In vivo regulation of increase in the blood-brain barrier permeability and increase in the amount of Evans blue permeated into the brain by SC79. SC79 was injected into tail veins of tumor-bearing animals at an administration dose of 5 mg/kg and 10 mg/kg, respectively. After 24 hours, an Evans blue solution was injected into tail veins at an administration dose of 5 mg/kg. After 4 hours, the intact brain of the nude mice was taken by cardiac perfusion. Panel A shows the result of distribution intensity of Evans blue in the brain tissue as qualitatively observed with a small animal live imaging instrument. Panel B shows the semi-quantitative result of the fluorescent signal of Evans blue.

As can be seen from the results shown in FIG. 10, as compared with the tumor-bearing control group, after the administration of SC79 for stimulus, the amount of Evans blue permeated into the brain is increased, which shows that the blood-brain barrier permeability is significantly increased. It indicates that SC79 can increase the blood-brain barrier permeability.

Male BABL/c nude mice (20±2 g) were used as the model animals. SC79 diluted with 0.2% injection grade Tween 80 solution was injected into tail veins at an administration dose of 5 mg/kg, 10 mg/kg. After 0.5 hour, and after 24 hours, an Evans blue solution was injected into tail veins at an administration dose of 5 mg/kg. After 4 hours, the intact brain of the nude mice was taken by cardiac perfusion. The distribution intensity of Evans blue in the brain tissue was qualitatively observed with a small animal live imaging instrument. The Results were shown in FIG. 11.

Figure 11:
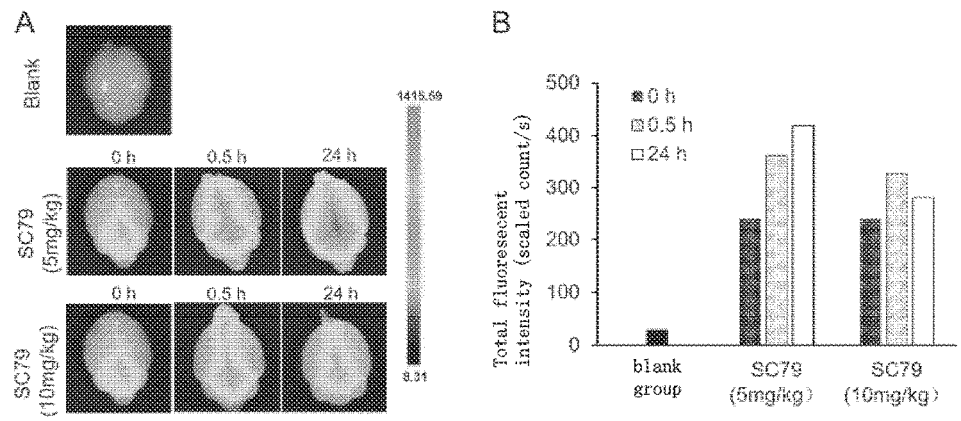
FIG. 11: In vivo time-dependent regulation of increase in the blood-brain barrier permeability by SC79. SC79 was injected into tail veins of tumor-bearing animals at an administration dose of 5 mg/kg and 10 mg/kg, respectively. After 0 hour, 0.5 hour, and 24 hours, an Evans blue solution was injected into tail veins at an administration dose of 5 mg/kg. After 4 hours, the intact brain of the nude mice was taken by cardiac perfusion. Panel A shows the result of distribution intensity of Evans blue in the brain tissue as qualitatively observed with a small animal live imaging instrument. Panel B shows the semi-quantitative result of the fluorescent signal of Evans blue.

As can be seen from the results shown in FIG. 11, 0.5 hour after the administration of SC79 for stimulus, the amount of Evans blue permeated into the brain is increased; 24 hours after the administration of SC79 for stimulus, the amount of Evans blue permeated into the brain is the highest. It indicates that SC79 has the most significant effect in modulating an increase in the blood-brain barrier permeability.

Male BABL/c nude mice (20+2 g) were used as the model animals. U87-luci glioma cells expressing luciferase were inoculated in the striatum area of nude mice at a concentration of $5 \times 10^5$ cells/5 µL by means of a brain stereotaxic instrument (inoculation coordinates, 0.8 mm on the anterior side of bregma, 2 mm on the right side, and 3 mm in depth), to construct an in situ glioma model. SC79 diluted with 0.2% injection grade Tween 80 solution was injected into tail veins at an administration dose of 5 mg/kg. After 24 hours, the Angiopep-2-modified glycolipid nano-delivery system encapsulated with near-infrared fluorescent probe DiR was injected into tail veins. After 4 hours, the intact brain of the nude mice was taken by cardiac perfusion. The distribution intensity of Angiopep-2-modified glycolipid nano-delivery system in the brain tissue was qualitatively observed with a small animal live imaging instrument. The Results were shown in FIG. 12.

Figure 12:
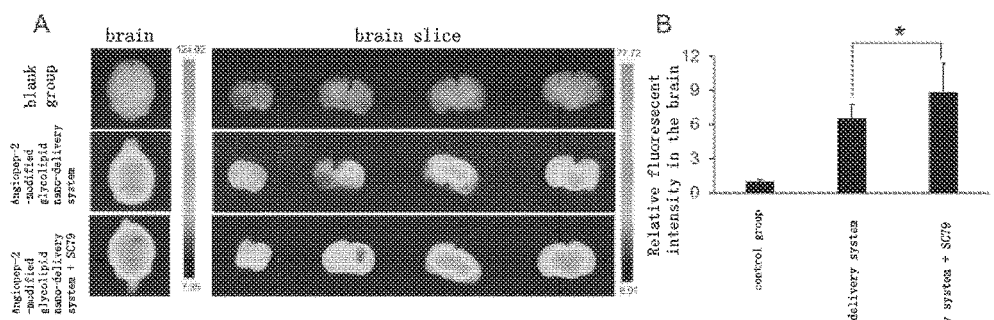
FIG. 12: Regulation of increase in the blood-brain barrier permeability and enhancement of distribution of Angiopep-2-modified glycolipid nano-delivery system in the brain by SC79. SC79 was injected into tail veins of tumor-bearing animals at an administration dose of 5 mg/kg. After 24 hours, the Angiopep-2-modified glycolipid nano-delivery system encapsulated with near-infrared fluorescent probe DiR was injected into tail veins. After 4 hours, the intact brain of the nude mice was taken by cardiac perfusion. Panel A shows the result of distribution intensity of Angiopep-2-modified glycolipid nano-delivery system encapsulated with near-infrared fluorescent probe DiR in the brain tissue as qualitatively observed with a small animal live imaging instrument. Panel B shows the semi-quantitative result of the fluorescent signal of the Angiopep-2-modified glycolipid nano-delivery system encapsulated with near-infrared fluorescent probe DiR (n=3).

As can be seen from the results shown in FIG. 12, as compared with the tumor-bearing control group, after the administration of SC79 for stimulus, the distribution of Angiopep-2-modified glycolipid nano-delivery system in the brain is increased. It indicates that SC79 can enhance the transportation efficiency of Angiopep-2-modified glycolipid nano-delivery system into the brain.

Example 7 Sequential Treatment of Glioma with SC79 and Angiopep-2-Modified Glycolipid Nano-Delivery System Male BABL/c nude mice (20±2 g) were used as the model animals. U87-luci glioma cells expressing luciferase were inoculated in the striatum area of nude mice at a concentration of $5 \times 10^5$ cells/5 µL by means of a brain stereotaxic instrument (inoculation coordinates, 0.8 mm on the anterior side of bregma, 2 mm on the right side, and 3 mm in depth), to construct an in situ glioma model. The Angiopep-2-modified glycolipid nano-delivery system was injected into tail veins at an administration dose of 10 mg/kg in terms of paclitaxel and 50 nM/kg in terms of siRNA. After 48 hours, a SC79 solution in Tween was injected into tail veins. After 24 hours, when regulation of the blood-brain barrier by SC79 reaches the highest, the Angiopep-2-modified glycolipid nano-delivery system was injected into tail veins for the second time. SC79 was injected into tail veins for three times in total. The Angiopep-2-modified glycolipid nano-delivery system was injected into tail veins for four times in total. Growth of glioma in situ was real-time monitored by a bioluminescent imaging technology. The Results were shown in FIG. 13.

Figure 13:
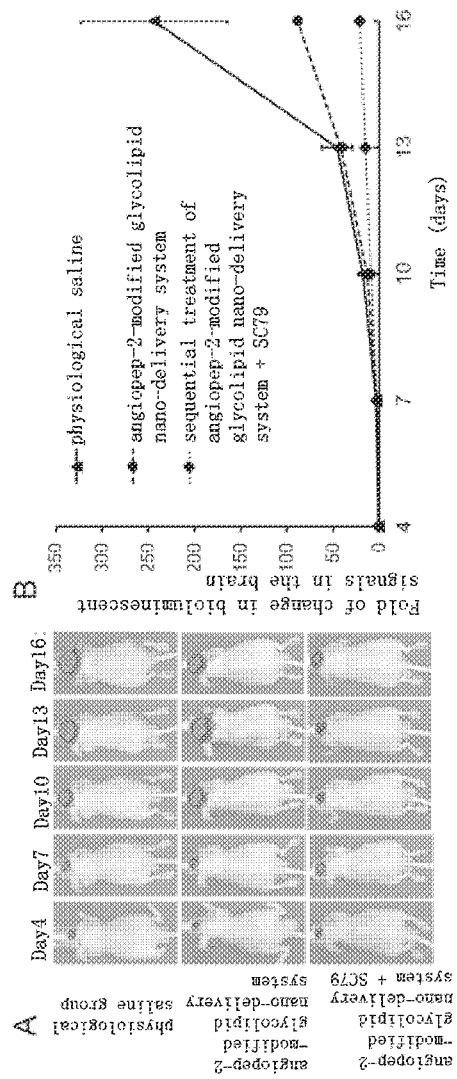
FIG. 13: Therapeutic effect of in vivo administration of SC79 24 hours in advance of the admistration of Angiopep-2-modified glycolipid nano-delivery system. The drug was administered on Day 4 of tumor-bearing. The Angiopep-2-modified glycolipid nano-delivery system was injected into tail veins at an administration dose of 10 mg/kg in terms of paclitaxel and 50 nM/kg in terms of siRNA. After 48 hours, SC79 was injected into tail veins of tumor-bearing animals at an administration dase of 5 mg/kg. After 24 hours, the Angiopep-2-modified glycolipid nano-delivery system was injected into tail veins for the second time. SC79 was injected into tail veins for three times in total. The Angiopep-2-modified glycolipid nano-delivery system was injected into tail veins for four times in total. Growth of glioma was in situ monitored by a bioluminescent imaging technology. Panel A qualitatively reflects the size of the brain tumor on Day 4, 7, 10, 13 and 16 of tumor-bearing. Panel B is a quantitative monitoring curve showing real-time growth of glioma (on Day 4, 7, 10, 13 and 16) (n=5). A physiological saline group was used as a control group.

As can be seen from the results shown in FIG. 13, as compared with a physiological saline control group and a group of treatment with the Angiopep-2-modified glycolipid nano-delivery system at alone, the sequential treatment with SC79 and Angiopep-2-modified glycolipid nano-delivery system can significantly inhibit the growth of glioma.

INDUSTRIAL APPLICABILITY

According to the present invention, a blood-brain barrier permeability regulator comprising SC79 or an analogue thereof as an active ingredient can be provided, which can increase the blood-brain barrier permeability, enhance the efficiency of transportation of a brain targeting drug delivery system, especially, an Angiopep-2-modified glycolipid nano-delivery system, into the brain. By the application of the blood-brain barrier permeability regulator in combination with a brain targeting drug delivery system, it is enabled to enhance the efficiency of transportation of a brain targeting drug delivery system into the brain, and thereby improve the therapeutic efficacy of the brain targeting drug delivery system in the treatment of brain diseases, and has a significantly superior technical effect. Therefore, the present invention has great applicability in the field of medicine.

---

---

The invention claimed is:

1. A method for increasing blood-brain barrier permeability and enhancing the efficiency of transportation into the brain of a brain targeting drug delivery system, comprising administering to a subject an effective amount of SC79, and administering to the subject an effective amount of the brain targeting drug delivery system.

2. The method of claim 1, wherein the brain targeting drug delivery system is an Angiopep-2-modified glycolipid nano-delivery system.

3. The method of claim 2, wherein the Angiopep-2-modified glycolipid nano-delivery system is an Angiopep-2-modified glycolipid nano-delivery system co-delivering paclitaxel and an siRNA.

4. The method of claim 3, wherein the siRNA comprises an siRNA having a nucleotide sequence as follows:

```
sense strand:
                                      (SEQ ID NO: 1)
5'-GUCUAUCAGCGCAGCUACUTT-3', antisense strand:
                                      (SEQ ID NO: 2)
5'-AGUAGCUGCGCUGAUAGACTT-3'.
```

5. The method of claim 1, wherein the brain targeting drug delivery system is administered 0.5 hour after the administration of the SC79.

6. The method of claim 1, characterized in that the brain targeting drug delivery system is administered 24 hours after the administration of the SC79.

7. A brain targeting drug delivery kit, comprising a combination of a blood-brain barrier permeability regulator and a brain targeting drug delivery system,
wherein the blood-brain barrier permeability regulator comprises SC79 as an active ingredient.

8. The kit of claim 7, wherein the brain targeting drug delivery system is an Angiopep-2-modified glycolipid nano-delivery system.

9. A method for treating a brain disease in a subject in need of the treatment, comprising administering to the subject an effective amount of a blood-brain barrier permeability regulator and an effective amount of a brain targeting drug delivery system,
wherein the blood-brain barrier permeability regulator comprises SC79 as an active ingredient.

10. The method of claim 9, wherein the brain targeting drug delivery system is an Angiopep-2-modified glycolipid nano-delivery system.

11. The method of claim 10, wherein the Angiopep-2-modified glycolipid nano-delivery system is an Angiopep-2-modified glycolipid nano-delivery system co-delivering paclitaxel and a siRNA.

12. The method of claim 11, wherein the siRNA comprises a siRNA having a nucleotide sequence as follows:

```
sense strand:
                                      (SEQ ID NO: 1)
5'-GUCUAUCAGCGCAGCUACUTT-3', antisense strand:
                                      (SEQ ID NO: 2)
5'-AGUAGCUGCGCUGAUAGACTT-3'.
```

13. The method of claim 9, wherein the brain targeting drug delivery system is administered 0.5 hour after the administration of the blood-brain barrier permeability regulator.

14. The method of claim 9, wherein the brain targeting drug delivery system is administered 24 hours after the administration of the blood-brain barrier permeability regulator.

15. The method of claim 9, wherein the brain disease is one or more selected from a group consisting of glioma, pituitary tumor, meningioma and metastatic brain tumor.

16. The method of claim 9, wherein the brain disease is glioma.

17. The method of claim 12, wherein the brain disease is glioma, and the blood-brain barrier permeability regulator and the brain targeting drug delivery system are sequentially administered.

* * * * *